US00PP29921P3

(12) United States Plant Patent
Hansen et al.

(10) Patent No.: US PP29,921 P3
(45) Date of Patent: Nov. 27, 2018

(54) ***COREOPSIS* PLANT NAMED 'ZESTY ZINGER'**

(50) Latin Name: *Coreopsis verticillata*
Varietal Denomination: Zesty Zinger

(71) Applicants: Hans A. Hansen, Zeeland, MI (US); Kevin A. Hurd, Austin, TX (US)

(72) Inventors: Hans A. Hansen, Zeeland, MI (US); Kevin A. Hurd, Austin, TX (US)

(73) Assignee: Walters Gardes Inc, Zeeland, MI (US)

( * ) Notice: Subject to any disclaimer, the term of this patent is extended or adjusted under 35 U.S.C. 154(b) by 43 days.

(21) Appl. No.: 15/530,129

(22) Filed: Dec. 5, 2016

(65) Prior Publication Data

US 2018/0160608 P1 Jun. 7, 2018

(51) Int. Cl.
*A01H 5/02* (2018.01)

(52) U.S. Cl.
USPC ..... Plt./417
CPC ..... *A01H 5/02* (2013.01)

(58) Field of Classification Search
USPC ..... Plt./417
See application file for complete search history.

*Primary Examiner* — Keith O. Robinson

(57) ABSTRACT

The new and distinct threadleaf *coreopsis* plant, *Coreopsis verticillata* plant named 'Zesty Zinger', with linear, foliage of bright-green, numerous flowers with ray petals with ray petals dark magenta lightening to ivory tips, blooming over a prolonged season from mid-summer until early fall. The new plant is useful as a specimen landscape plant, mass planting, container plant and cut flower.

1 Drawing Sheet

Botanical designation: *Coreopsis verticillata.*
Cultivar denomination: 'Zesty Zinger'.

BACKGROUND OF THE PLANT

The present invention relates to the new and distinct threadleaf *coreopsis* herein also referred to as *Coreopsis* 'Zesty Zinger', by the cultivar name 'Zesty Zinger', or as the new plant. The new plant was selected by Hans Hansen in June of 2011 from an open pollination of an isolated block of plants all derived from the unreleased proprietary seedling with breeder code the K9-01-04 which is an open pollinated seedling from 'Route 66' U.S. Plant Pat. No. 20,609 harvested on Oct. 19, 2010 at a wholesale perennial nursery in Zeeland, Mich. After passing the initial evaluation the single seedling selected from this group of seedlings was initially given the breeder code HK10-02-10. It was then, isolated and compared in subsequent years to other *coreopsis* and subsequently found to be different from all cultivars known to the discoverers.

Asexual propagation at the same nursery in Zeeland, Mich., USA by shoot tip cuttings has shown 'Zesty Zinger' to be stable and reproduce true to type in successive generations.

No plants of *Coreopsis* 'Zesty Zinger' have been sold, by this or any name, in this country or anywhere in the world, prior to the filing of this application, nor has any disclosure of the new plant been made prior to the filing of this application with the exception of that which may have been disclosed within one year of the filing date of this application and was either derived directly or indirectly from the inventors.

SUMMARY OF THE PLANT

*Coreopsis* 'Zesty Zinger' has not been observed in all possible environmental conditions. The phenotype may vary slightly with changes in environments such as light intensity, fertility, water availability, etc. without, however any variation in genotype.

*Coreopsis* 'Zesty Zinger' is distinct from all cultivars known to the inventors in the following traits:

1. Narrow foliage with compact height and dense habit.
2. Heavy flowering with ray petals dark magenta lightening to ivory tips.
3. Flowers produced tightly and densely above the thin, bright-green foliage.
4. Long flowering period beginning with concentration in early-summer and continuing until early fall.

*Coreopsis* 'Zesty Zinger' is most similar to 'Route 66' U.S. Plant Pat. No. 20,609, 'Autumn Blush' U.S. Plant Pat. No. 18,184, and 'Red Shift' U.S. Plant Pat. No. 20,412. 'Red Shift' produces ray flower petals that have a narrower red eye, the distal petal portion more cream and the foliage is broader than the new plant. Both 'Route 66' and 'Autumn Blush' have ray flower petals with narrower red eye and the distal petal portion is more creamy-yellow colored than the ivory distal portion of 'Zesty Zinger'. No plants of the female parent were saved, so no mature plant comparison could be made.

BRIEF DESCRIPTION OF THE DRAWINGS

The color drawings illustrate the overall characteristics of *Coreopsis* 'Zesty Zinger' as a three-year-old plant. The colors are as true as reasonably possible given the technology available. The color values may vary slightly depending on light intensity and quality.

FIG. 1 shows a close-up of several flowers of the new plant.

DETAILED BOTANICAL DESCRIPTION

The following description is based on a two-year-old plant growing in a full-sun trial garden in Zeeland, Mich., USA. Environmental conditions for the growing season daytime temperatures range between 12 and 30° C., and night temperatures range between 6 and 19° C. Except for ordinary dictionary color usage, color references are according to The Royal Horticultural Society Colour Chart, 2001 edition.

Parentage: Female or seed parent K9-01-04 (not patented) which is a selfed selection of 'Route 66' U.S. Plant Pat. No. 20,609; male or pollen parent unknown;

Asexual propagation: Cuttings, about 10 to 14 days to initiate roots; time to finish as # 1 field grown size about 9 months;

Plant habit: Dense axillary branches; rounded, herbaceous perennial mound; about 45 cm wide and about 30 cm tall;

Roots: Thin; fibrous; heavily branched; color variable with soil type, nearest RHS NN155A;

Leaves: Linear, opposite, sessile, glabrous abaxial and adaxial; margins entire; acute apex; base attenuate; average about 2.5 cm long and 1.8 mm wide; about six leaves per stem;

Leaf color: Young expanding leaves adaxial and abaxial nearest RHS 144A; mature leaves adaxial and abaxial between RHS 137A and RHS 138A;

Veins: Pinnate; only abaxial midvein obvious;

Abaxial midveins color: Same as surrounding leaf;

Flower: Composite consisting of ray and disk florets; on terminal branches; about 4.3 cm diameter, about 1.3 cm tall from lower involucral bracts to top of disk florets; capitulum head about 6.0 mm across and about 5.0 mm tall; attitude outwardly to slightly upwardly;

Flower fragrance: None detected;

Phyllary: Five sepals; linear; margin entire, ciliolate; rounded apex, truncate base; glabrous abaxial and adaxial; about 4.5 mm long and 1.0 mm wide at base;

Phyllary color: Between RHS 137A and RHS 138A on both abaxial and adaxial;

Flowering period: Early summer until early fall, for about 12 weeks; producing over 50 flowers per stem and over 350 flowers per plant;

Flower longevity: 4 to 6 days;

Flower buds: Globose; while petals still upright — about 5.0 mm wide and 10.0 mm tall;

Flower bud color: Petal color nearest RHS 1A;

Stem: Terete; heavily branched; glaucous, wiry, upright attitude, strong; about 3.0 mm wide at base and 26.0 cm long; about five to seven nodes, average internode spacing about 4.3 cm;

Stem color: Lower stem between RHS 199A and RHS 200A and upper stem nearest RHS 137A; about two to three inflorescences per lateral branch;

Branches: Branches extending slightly above main stems and covering up earlier flowers; typically about 10 branches per main stem;

Peduncle: Terete; glaucous; stiff, strong; upright; about 26.0 c cm long and 3.0 mm diameter at base;

Pedicel: Terete; glaucous, thin, wiry, strong; to about 5.0 cm long and about 0.7 mm diameter, average about 3.5 cm in long and about 0.7 mm diameter; attitude upright;

Pedicel color: Nearest RHS 137C;

Ray florets: Typically eight per inflorescence; imperfect; sterile;

Ligule: Usually 8 per flower head; oblong elongate, glabrous; apex typically two-notched, margin entire; base narrowly attenuate to form claw; opening nearly flat to form about 180° angle; parallel veined; glabrous adaxial and adaxial; about 2.2 cm long and about 8.0 mm wide; basal corolla tube about 1.5 mm to 3.0 mm long and about 0.8 mm diameter; lacking stamens and pistils;

Ligule color: Adaxial apical one-third nearest RHS 155D, middle one-third to claw more red than RHS 187A, darker than RHS 61A and lighter than RHS N77A, basal claw nearest RHS 1B; abaxial apical one their nearest RHS 155D, middle nearest RHS 161D with purple-red tinting darker than RHS 61A, near base between RHS 163B and RHS 163C with purple-red tinting darker than RHS 61A, basal claw nearest RHS 155D;

Receptacle: Semi-domed shaped; about 6.0 mm diameter and 5.0 mm tall; color nearest RHS 145B;

Disk florets: 30 to 38 per head; consisting of five tepals fused in the base forming tube; perfect; actinomorphic; size about 4.0 mm long by 1.2 mm wide distally;

*Tepals*.—Five; 4.0 mm long and 1 mm wide, fused in the basal 3.0 mm; acute apex; glabrous abaxial and adaxial.

*Tepal color*.—Adaxial base neatest RHS 14A, apex nearest RHS 187A; abaxial base nearest RHS 14A, middle and apex between RHS 187B and RHS 187C.

*Staminal tube*.—Five connate stamens, about 2.0 mm long and about 0.5 mm diameter; color nearest RHS 187A.

*Anther*.—About 1 mm long, nearest RHS 187A.

*Pollen*.—Not observed.

*Style*.—About 5.0 mm long, curled 360° in apical 1.5 mm; color nearest RHS 13A.

*Stigma*.—Split in half and curling back as it matures; color nearest RHS 17B.

Seed: Linear with slight curve, with acute apex and truncate base; glabrous abaxial and adaxial surfaces, margin slightly sulcate; about 5.5 mm long, about 2.2 mm across;

Seed color: Variable, nearest RHS 202A; *Coreopsis verticillata* 'Zesty Zinger' is tolerant of winter temperatures as low as −20° C. and summer temperatures as high as 40° C. Once established it is also tolerant of dry summer conditions but does best with ample moisture and good drainage. It is not known to be resistant of diseases and pest that are common to other *Coreopsis* cultivars. The new plant may be susceptible to Powdery mildew (*Sphaerotheca macularis*), bacterial blight (*Pseudomonas cichorii*), Stem rot (*Sclerotium rolfsii*), Leaf spot (*Botrytis cinerea*) and Wilt (*Verticillium alboatrum*) but such diseases have not been observed.

It is claimed:

1. The new and distinct cultivar of *Coreopsis* plant named 'Zesty Zinger' as described and illustrated and useful as a specimen landscape plant, mass planting or cut flower.

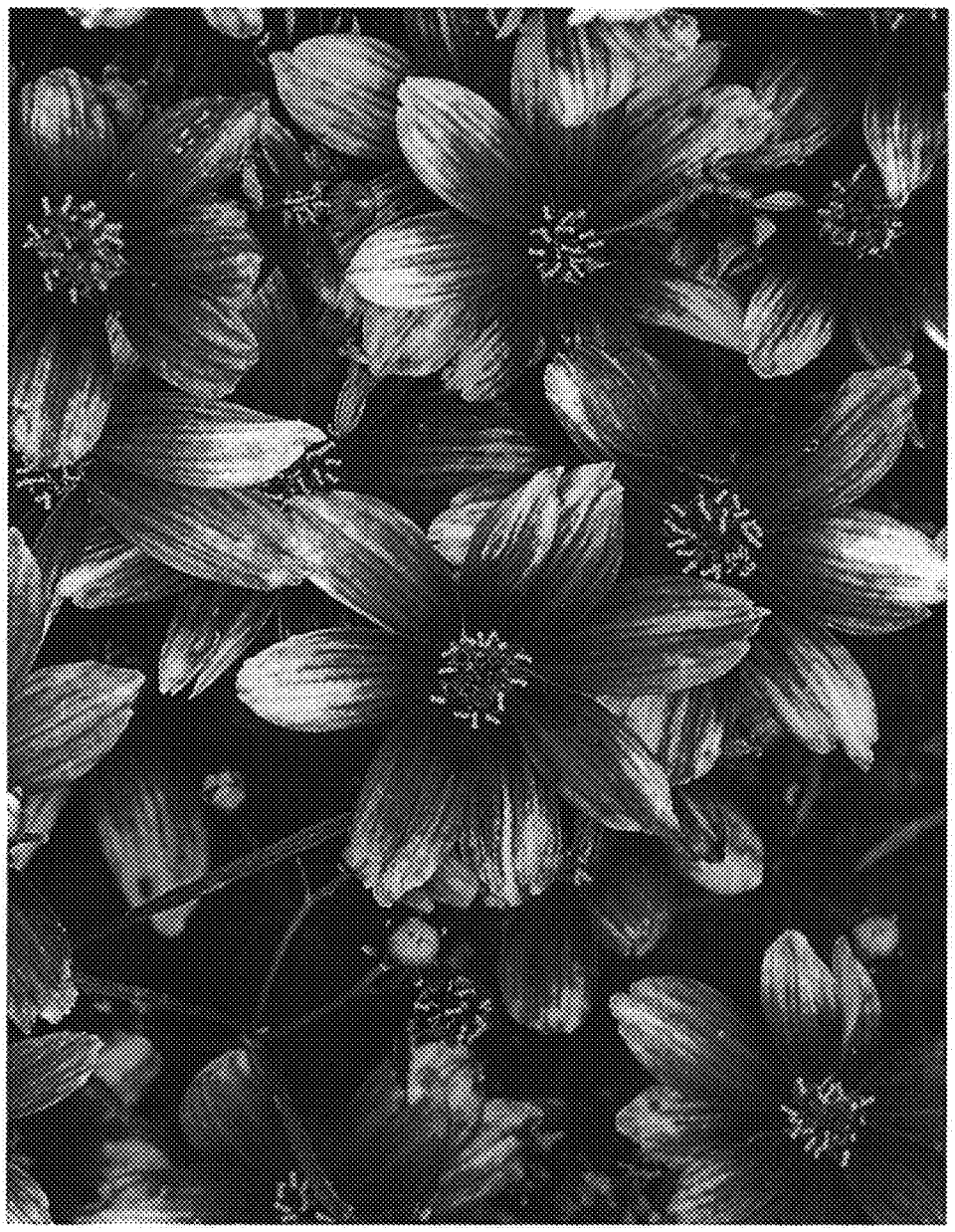

* * * * *